US009538932B2

(12) United States Patent
Suto (10) Patent No.: US 9,538,932 B2
(45) Date of Patent: Jan. 10, 2017

(54) ELECTROCARDIOGRAM MEASURING APPARATUS AND SYNTHESIZED ELECTROCARDIOGRAM GENERATING METHOD

(71) Applicant: Nihon Kohden Corporation, Shinjuku-ku, Tokyo (JP)

(72) Inventor: Jiro Suto, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 14/524,424

(22) Filed: Oct. 27, 2014

(65) Prior Publication Data

US 2015/0119734 A1    Apr. 30, 2015

(30) Foreign Application Priority Data

Oct. 28, 2013 (JP) ................................. 2013-223514

(51) Int. Cl.
*A61B 5/0402* (2006.01)

(52) U.S. Cl.
CPC ....... *A61B 5/04028* (2013.01); *A61B 5/04021* (2013.01)

(58) Field of Classification Search
CPC .................. A61B 5/04028; A61B 5/04021
See application file for complete search history.

(56) References Cited

U.S. PATENT DOCUMENTS

| 2002/0045837 | A1 | 4/2002 | Wei et al. |
| 2010/0305461 | A1 | 12/2010 | Wei |
| 2012/0029371 | A1 | 2/2012 | Wei |

FOREIGN PATENT DOCUMENTS

| EP | 1304958 B1 | 11/2008 |
| JP | 4153950 B2 | 9/2008 |
| JP | 4587008 B2 | 11/2010 |
| JP | 2012-029904 A | 2/2012 |

OTHER PUBLICATIONS

Extended European Search Report dated Mar. 23, 2015 issued by European Patent Office in counterpart European Application No. 14190564.6.
Hussein et al., "A Novel Neural-Network Model for Deriving Standard 12-Lead ECGs From Serial Three-Lead ECGs: Application to Self-Care", IEEE Transactions on Information Technology in Biomedicine, May 1, 2010, 8 pages total, vol. 14 No. 3, IEEE Service Center, Los Alamitos, California, USA.

*Primary Examiner* — Joseph Dietrich
(74) *Attorney, Agent, or Firm* — Sughrue Mion, PLLC (57) ABSTRACT

An electrocardiogram measuring apparatus includes: a population coefficient calculating unit which calculates: first population coefficients; and second population coefficients; a personal coefficient calculating unit which calculates: first personal coefficients; and second personal coefficients; and a lead deriving unit which: calculates first personal coefficients of a specific subject based on: a relationship between a magnitude of a ratio of the first population coefficients to the second population coefficients, and a magnitude of a ratio of the first personal coefficients to the second personal coefficients; and second personal coefficients of the specific subject which are calculated based on A leads of the specific subject, the A leads being acquired by electrocardiogram measurement; and synthesizes B leads of the specific subject by using the first personal coefficients of the specific subject.

8 Claims, 2 Drawing Sheets

ELECTROCARDIOGRAM MEASURING APPARATUS AND SYNTHESIZED ELECTROCARDIOGRAM GENERATING METHOD

CROSS-REFERENCE TO RELATED APPLICATION(S)

This application is based upon and claims the benefit of priority from prior Japanese patent application No. 2013-223514, filed on Oct. 28, 2013, the entire contents of which are incorporated herein by reference.

BACKGROUND

The presently disclosed subject matter relates to an electrocardiogram measuring apparatus and a synthesized electrocardiogram generating method.

In the case where a standard 12-lead electrocardiogram is acquired from the patient, ten electrodes connected to an electrocardiograph functioning as an electrocardiogram measuring apparatus are used, and attached to six places for measuring chest leads, and four places for measuring limb leads, respectively. Based on cardiac potentials detected from the ten electrodes, then, the electrocardiograph calculates and outputs six limb lead waveforms (I, II, III, aVR, aVL, and aVF) of standard 12 leads, and six chest lead waveforms (V1, V2, V3, V4, V5, and V6) of standard 12 leads.

Usually, relationships between lead waveforms for obtaining a standard 12-lead electrocardiogram and cardiac potentials in measurement portions are as follows:

lead I: $vL-vR$
lead II: $vF-vR$
lead III: $vF-vL$
lead aVR: $vR-(vL+vF)/2$
lead aVL: $vL-(vR+vF)/2$
lead aVF: $vF-(vL+vR)/2$
lead V1: $v1-(vR+vL+vF)/3$
lead V2: $v2-(vR+vL+vF)/3$
lead V3: $v3-(vR+vL+vF)/3$
lead V4: $v4-(vR+vL+vF)/3$
lead V5: $v5-(vR+vL+vF)/3$
lead V6: $v6-(vR+vL+vF)/3$ where v represents a potential which is detected in each of the electrode attachment positions.

Diagnosis which is to be performed on a heart disease of the patient by using such many electrodes is enabled in a state where the patient is kept quiet, only in a large fully equipped hospital or the like.

However, in the case where home care or emergency medicine is performed, for example, it is often difficult, from the viewpoint of the condition of the patient, to use many electrodes and attach the electrodes to adequate positions of the body surface of the living body. Moreover, there is a case where a multi-channel signal for obtaining many lead waveforms is hardly transmitted. In such a case, usually, the number of channels through which signals for an electrocardiogram can be transmitted is about one or two (one or two leads). Diagnosis of a heart disease is performed by using two to four electrodes at most and measuring several lead waveforms of standard 12-lead waveforms.

Concerning this, there are a method of constructing a synthesized 12-lead electrocardiogram, and an electrocardiogram inspection apparatus in which a standard 12-lead electrocardiogram that enables diagnosis and treatment of various heart diseases to be properly performed is reconstructed by a subset of a lead system having a minimum number of leads required for obtaining a standard 12-lead electrocardiogram (see Japanese Patent No. 4,587,008).

In the method of constructing a synthesized 12-lead electrocardiogram which is disclosed in Japanese Patent No. 4,587,008, leads I and II which are limb leads in the case where a standard 12-lead electrocardiogram is to be obtained, and leads V1 and V5 or V6 which are two of chest leads are used as a subset of a lead system consisting of a minimum number of channels. These leads enable leads III and aV (leads aVR, aVL, and aVF) to be obtained by calculation based on the above-described inherent relationships of the leads. The remaining ones of the chest leads, or leads V2, V3, V4, and V6 or V5 are synthesized by calculation using conversion coefficients (derivation matrix) which are produced in consideration of relationships between potential-lead vectors and cardiac vectors.

In a synthesized 12-lead electrocardiogram which is obtained as described above from inherent relationships of leads and produced conversion coefficients, a subset of a lead system for a related-art standard 12-lead electrocardiogram is used, and, in attachment of electrodes, therefore positioning to predetermined portions can be performed easily and surely. Consequently, the attachment work does not require a lot of skill. Moreover, an accurate standard 12-lead electrocardiogram can be reconstructed, and therefore various heart diseases can be diagnosed and treated properly.

In a related-art electrocardiograph, therefore, an abnormality of electrocardiogram waveforms can be checked and diagnosed not only in the case where a standard 12-lead electrocardiogram is obtained from six limb leads and six chest leads by using ten electrodes, but also in the case where an accurate synthesized 12-lead electrocardiogram is synthesized by using the method disclosed in Japanese Patent No. 4,587,008.

Another case where a synthesized electrocardiogram related to an application of standard 12 leads is necessary will be described. In the above-described standard 12-lead electrocardiogram, when it is applied to diagnosis of myocardial infarction, it is easy to check and diagnose an abnormality of electrocardiogram waveforms with respect to the anterior/lateral wall in which blockage of the coronary arteries supplying the blood flow to the cardiac muscle may occur. With respect to the posterior or right posterior wall, however, the sensitivity is low because positions of electrodes are remote from the heart. According to a research paper, ST elevations of many posterior acute myocardial infarctions (AMIs) appear in V7, V8, and V9. In a standard 12-lead electrocardiogram, therefore, ST elevations are often overlooked. It has been proposed that, if necessary, the above-described additional leads are measured. In the case where a standard electrocardiograph is used, however, the measurement must be conducted two times, and particularly V7, V8, and V9 are on the back side and therefore hardly measured. Therefore, an electrocardiograph having an additional lead function and a method of deriving an additional-lead electrocardiogram have been proposed in which, by using measurement signals of a standard 12-lead electrocardiogram, electrocardiogram waveforms of V7, V8, and V9 are synthesized for diagnosis of inferior wall infarction, and those of V3R, V4R, and V5R are synthesized for diagnosis of right ventricular infarction, whereby accurate diagnosis information can be provided (see Japanese Patent No. 4,153, 950).

In the technique disclosed in Japanese Patent No. 4,153, 950, however, electrocardiogram waveforms of portions to which an electrode is not attached, i.e., waveforms of synthesized electrocardiograms are calculated by using conversion coefficients indicating relationships between measured lead vectors (lead vectors of portions to which an electrode is attached) and synthesized lead vectors (lead vectors of portions to which an electrode is not attached), and hence the accuracy of the conversion coefficients affects synthesized electrocardiograms of the subject, and the accuracy of diagnosis of a heart disease. As a conversion coefficient, usually, the average value (hereinafter, referred to as the population coefficient) of a plurality of conversion coefficients which are obtained from a large unspecified number of persons. A population coefficient can statistically assure a certain kind of conversion accuracy, but is hardly regarded as an optimum conversion coefficient for the subject himself/herself. Therefore, the difference between a synthesized electrocardiogram and "true values" (values which would be obtained if measured) cannot be sometimes satisfied from a clinical viewpoint.

In view of the circumstances, a synthesized electrocardiogram generating system has been proposed in which a conversion coefficient (hereinafter, referred to as the personal coefficient) of the subject himself/herself is previously stored in a database according to the type of a synthesized electrocardiogram, and the conversion coefficient is read out as required, whereby a synthesized electrocardiogram can be acquired (for example, see JP-A-2012-029904).

In the synthesized electrocardiogram generating system of JP-A-2012-029904, in order to calculate personal coefficients for deriving desired leads, however, leads of arbitrary portions of the subject himself/herself must be previously measured, and therefore there is a problem in that the system is cumbersome and burdensome.

SUMMARY

The presently disclosed subject matter may provide an electrocardiogram measuring apparatus and a synthesized electrocardiogram generating method in which the accuracy of synthesized leads can be sufficiently ensured while avoiding the burden of previously measuring leads of arbitrary portions of the subject himself/herself.

The electrocardiogram measuring apparatus may comprise: a lead potential measuring unit which is configured to measure lead potentials of living body portions; a lead waveform calculating unit which is configured to calculate a plurality of lead waveforms based on the measured lead potentials; a population coefficient calculating unit which is configured to calculate: first population coefficients for a population of a predetermined number of persons which synthesize additional B leads (B is an integer of one or more) from A leads (A is an integer of four or more) containing a predetermined lead waveform in the plurality of lead waveforms; and second population coefficients for the population which synthesize additional D leads (D is A−C) from C leads (C is an integer of three or more and (A−1) or less) being smaller in number of lead waveforms than the A leads, by using the predetermined lead waveform of the A leads; a personal coefficient calculating unit which is configured to calculate: first personal coefficients for each person of the population which synthesize the B leads from the A leads; and second personal coefficients for each person of the population which synthesize the D leads from the C leads; and a lead deriving unit which is configured to: calculate first personal coefficients of a specific subject based on: a relationship between a magnitude of a ratio of the first population coefficients to the second population coefficients, and a magnitude of a ratio of the first personal coefficients to the second personal coefficients; and second personal coefficients of the specific subject which are calculated based on A leads of the specific subject, the A leads being acquired by electrocardiogram measurement; and synthesize B leads of the specific subject by using the first personal coefficients of the specific subject.

The lead deriving unit may be configured to: calculate a regression formula for the first personal coefficients to the second personal coefficients when points which are expressed by the first and second personal coefficients for each person of the population are plotted on an XY plane; and apply the second personal coefficients of the specific subject to the regression formula to calculate the first personal coefficients of the specific subject.

The A leads may be 12 leads containing six limb lead waveforms (I, II, III, aVR, aVL, and aVF), and six chest lead waveforms (V1, V2, V3, V4, V5, and V6), and the B leads may be six leads containing lead waveforms of V7, V8, V9, V3R, V4R, and V5R.

The lead potential measuring unit may be configured to measure lead potentials in 18 measurement portions of an electrocardiogram, and the lead waveform calculating unit may be configured to calculate 18 lead waveforms based on the measured 18 lead potentials.

The first population coefficients and the second population coefficients may be stored in a population coefficient database, and the first personal coefficients and the second personal coefficients may be stored in a personal coefficient database.

The synthesized electrocardiogram generating method may comprise: measuring lead potentials of living body portions, and calculating a plurality of lead waveforms based on the measured lead potentials; calculating: first population coefficients for a population of a predetermined number of persons which synthesize additional B leads (B is an integer of one or more) from A leads (A is an integer of four or more) containing a predetermined lead waveform in the plurality of lead waveforms; and second population coefficients for the population which synthesize additional D leads (D is A−C) from C leads (C is an integer of three or more and (A−1) or less) being smaller in number of lead waveforms than the A leads, by using the predetermined lead waveform of the A leads; calculating: first personal coefficients for each person of the population which synthesize the B leads from the A leads; and second personal coefficients for each person of the population which synthesize the D leads from the C leads; calculating a relationship between a magnitude of a ratio of the first population coefficients to the second population coefficients, and a magnitude of a ratio of the first personal coefficients to the second personal coefficients; acquiring A leads of a specific subject by electrocardiogram measurement, and calculating second personal coefficients of the specific subject based on the A leads of the specific subject; calculating first personal coefficients of the specific subject based on the relationship and the second personal coefficients of the specific subject; and deriving B leads of the specific subject by using the first personal coefficients of the specific subject.

In a process of calculating the first personal coefficients of the specific subject, a regression formula for the first personal coefficients to the second personal coefficients when points which are expressed by the first and second personal coefficients for each person of the population are plotted on an XY plane is calculated, and the second personal coefficients of the specific subject is applied to the regression formula to calculate the first personal coefficients of the specific subject.

There may be provided a synthesized electrocardiogram generating program causing an electrocardiogram measuring apparatus to execute the synthesized electrocardiogram generating method.

There may be provided a non-transitory computer-readable recording medium storing the synthesized electrocardiogram generating program.

DETAILED DESCRIPTION OF EXEMPLARY EMBODIMENTS

In an embodiment, it is assumed that personal coefficients of a specific subject who is to be subjected to measurement of an electrocardiogram are correlated with the population coefficients of a population of a predetermined number of persons, and additional leads of the specific subject are synthesized from measured leads which are acquired by measuring an electrocardiogram of the specific subject. Then, a synthesized electrocardiogram in which synthesized lead waveforms are added to measured lead waveforms is generated. The term "patient" is used as a specific example of a subject who is to be subjected to measurement of an electrocardiogram. The subject means not only a patient who is examined in a hospital, but also a user of a facility other than a hospital, such as a detection center or clinic in which a physical examination is performed, or an ordinary house.

It is a matter of course that the electrocardiogram measuring apparatus and synthesized electrocardiogram generating method and program of the embodiment can be applied to 18 types (type A to type R) of synthesized electrocardiograms which will be described below. In addition to the 18 synthesized electrocardiogram types, the embodiment can be applied also to a synthesized electrocardiogram type which is specific to the patient (custom-made synthesized electrocardiogram type), and which can generate synthesized electrocardiograms of arbitrary portions effective in diagnosing a heart diseases of the patient.

In synthesized additional-lead electrocardiograms (synthesized lead electrocardiograms for Brugada syndrome diagnosis), V1+, V2+, V1++, and V2++ represent portions which are effective in diagnosing a heart disease of the patient. The portion V1+ is a portion on the first intercostal space intercostal space of a lead V1, V2+ is a portion on the first intercostal space of a lead V2, V1++ is a portion on the second intercostal space of the lead V1, and V2++ is a portion on the second intercostal space of the lead V2. When synthesized electrocardiograms of the portions V1+, V2+, V1++, and V2++ are acquired, the diagnostic accuracy of a heart disease called Brugada syndrome is improved.

A synthesized mapping electrocardiogram (160-lead mapping electrocardiogram) generates electrocardiograms in 160 places on the body surface of the patient. The synthesized mapping electrocardiogram (160-lead mapping electrocardiogram) can easily obtain a synthesized electrocardiogram in an arbitrary portion, and therefore any heart disease of a patient having a unique heart can be accurately diagnosed.

A. Synthesized 12-Lead Electrocardiograms (1) V1, V3, V5, and V6 are synthesized from four leads I, II, V2, and V4 (type A)

(2) V2, V3, V5, and V6 are synthesized from four leads I, II, V1, and V4 (type B)

(3) V1, V3, V4, and V6 are synthesized from four leads I, II, V2, and V5 (type C)

(4) V2, V3, V4, and V6 are synthesized from four leads I, II, V1, and V5 (type D)

(5) V1, V3, V4, and V5 are synthesized from four leads I, II, V2, and V6 (type E)

(6) V2, V3, V4, and V5 are synthesized from four leads I, II, V1, and V6 (type F)

B. Synthesized Additional-Lead Electrocardiograms (18-Lead Electrocardiograms)

(7) V7, V8, V9, V3R, V4R, and V5R are synthesized from 12 leads I, II, and V1 to V6 (type G).

(8) V7, V8, V9, V3R, V4R, V5R, and V6R are synthesized from 12 leads I, II, and V1 to V6 (type H).

(9) V7, V8, V9, V3R, V4R, V5R, and V6R are synthesized from four leads I, II, V1, and V4 (type I).

(10) V7, V8, V9, V3R, V4R, V5R, and V6R are synthesized from four leads I, II, V2, and V5 (type J).

(11) V7, V8, V9, V3R, V4R, V5R, and V6R are synthesized from four leads I, II, V1, and V5 (type K).

(12) V7, V8, V9, V3R, V4R, V5R, and V6R are synthesized from four leads I, II, V2, and V6 (type L).

C. Synthesized Additional-Lead Electrocardiograms (Synthesized Lead Electrocardiograms for Brugada Syndrome Diagnosis)

(13) V1+, V2+, V1++, and V2++ are synthesized from 12 leads I, II, and V1 to V6 (type M).

(14) V1+, V2+, V1++, and V2++ are synthesized from four leads I, II, V1, and V4 (type N).

(15) V1+, V2+, V1++, and V2++ are synthesized from four leads I, II, V2, and V5 (type O).

(16) V1+, V2+, V1++, and V2++ are synthesized from four leads I, II, V1, and V5 (type P).

(17) V1+, V2+, V1++, and V2++ are synthesized from four leads I, II, V2, and V6 (type Q).

D. Synthesized Mapping Electrocardiogram (160-Lead Mapping Electrocardiogram)

(18) A body-surface 8×20 potential mapping is synthesized from 12 leads I, II, and V1 to V6 (type R).

Hereinafter, an embodiment of the electrocardiogram measuring apparatus and synthesized electrocardiogram generating method and program of the presently disclosed subject matter will be described with reference to the accompanying drawings. Although, in the embodiment, an example in which an electrocardiograph is used as an electrocardiogram measuring apparatus will be described, a Holter electrocardiograph, a biological information monitor, or the like may be used in place of an electrocardiograph. Alternatively, a personal computer may be connected to such an apparatus to configure an electrocardiogram measuring apparatus. In the figures, the identical members are denoted by the same reference numerals.

Figure 1:
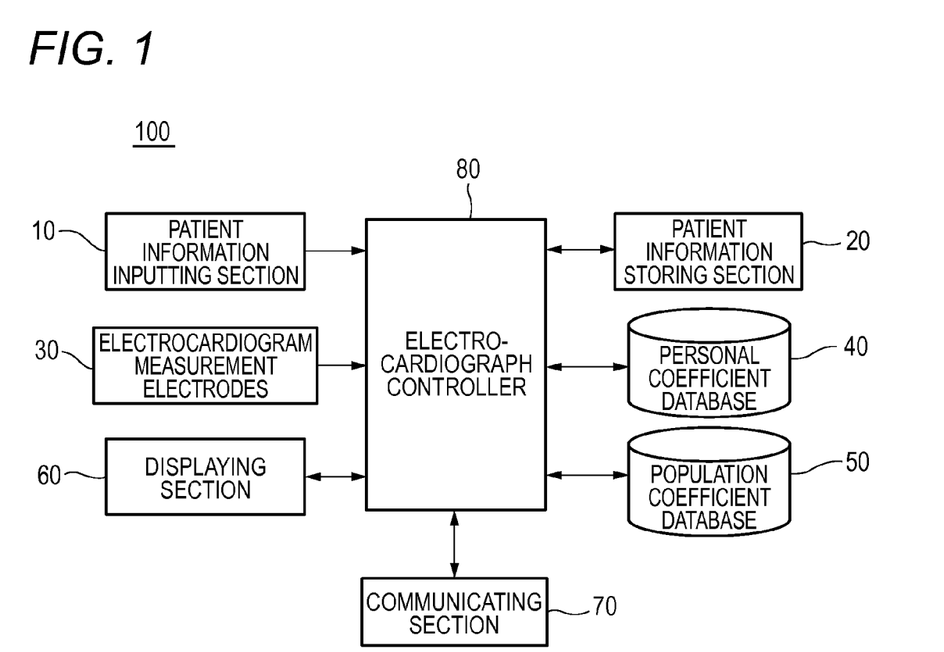
FIG. 1 is a block diagram schematically showing the configuration of an electrocardiograph of an embodiment of the presently disclosed subject matter.
Figure 2:
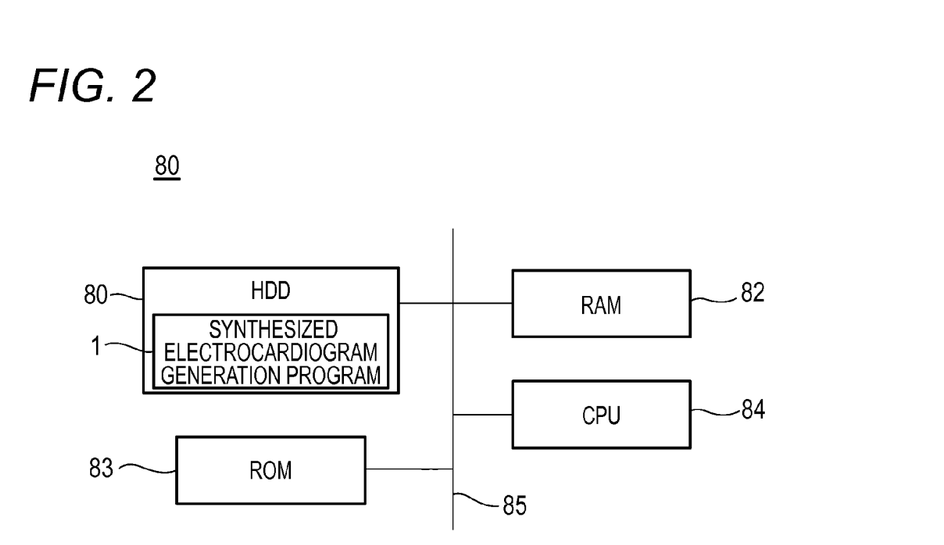
FIG. 2 is a block diagram schematically showing the configuration of an electrocardiograph controller shown in FIG. 1.

FIG. 1 is a block diagram schematically showing the configuration of an electrocardiograph which is an electrocardiogram measuring apparatus of an embodiment of the presently disclosed subject matter, and FIG. 2 is a block diagram schematically showing the configuration of an electrocardiograph controller shown in FIG. 1.

As shown in FIG. 1, the electrocardiograph 100 of the embodiment has a patient information inputting section 10, a patient information storing section 20, electrocardiogram measurement electrodes 30, a personal coefficient database 40, a population coefficient database 50, a displaying section 60, a communicating section 70, and the electrocardiograph controller 80.

The patient information inputting section 10 receives an input of information of the patient. The patient information inputting section 10 includes an inputting device such as a keyboard, a pointing device, or a touch panel. An operator who is a medical person operates the inputting section to input patient information such as the ID, name, age, and sex of the patient. The input patient information is transmitted to the patient information storing section 20.

The patient information storing section 20 stores the patient information input through the patient information inputting section 10, patient lead data, and the like. Specifically, the patient information storing section 20 includes a storage device such as a hard disk drive, and stores the patient information which is received from the patient information inputting section 10, such as the ID, name, age, and sex of the patient, the type of a measured electrocardiogram, that of a synthesized electrocardiogram, measured lead data, synthesized lead data of the patient, and the like.

The electrocardiogram measurement electrodes 30 are electrodes which are to be attached to the body surface of the patient to measure lead potentials of living body portions. In the case where a standard 12-lead electrocardiogram is to be measured, ten electrodes connected to the electrocardiograph controller 80 are used, and the electrodes are attached to six places for measuring chest leads, and four places for measuring limb leads, respectively. The electrocardiogram measurement electrodes 30 function as the lead potential measuring unit.

The personal coefficient database 40 is a database in and from which the personal coefficients of the patient are stored and read out. The personal coefficients are conversion coefficients which are acquired from the patient in order to generate a synthesized electrocardiogram of the patient, and which are inherent in the patient, and used for calculating synthesized leads from measured leads obtained in electrocardiogram measurement. In the embodiment, in advance of electrocardiogram measurement of a specific patient who is the target for electrocardiogram measurement, personal coefficients are calculated with respect to a population of a predetermined number of persons, and then stored in the personal coefficient database 40.

Also the personal coefficients which are calculated based on a result of the electrocardiogram measurement of the specific patient are stored in the personal coefficient database 40.

The population coefficient database 50 is a database in and from which the population coefficients are stored and read out. A population coefficient is the average value of a plurality of personal coefficients which, in order to generate a synthesized electrocardiogram of a patient, are acquired from a large unspecified number of persons belonging to a statistically significant population, and used for calculating synthesized leads from measured leads obtained in electrocardiogram measurement. In the embodiment, in advance of electrocardiogram measurement of a specific patient who is the target for electrocardiogram measurement, electrocardiograms of a population of a predetermined number of persons are measured, and population coefficients are calculated based on a result of the measurement, and then stored in the population coefficient database.

A synthesized electrocardiogram can be generated by using population coefficients or personal coefficients based on the following principle. The principle will be described by exemplifying a synthesized 12-lead electrocardiogram of the type C above.

In the case where a synthesized 12-lead electrocardiogram of the type C is to be generated, a total of six electrocardiogram measurement electrodes are attached to the body surface of a patient. The electrocardiogram measurement electrodes are attached to four places of left and right arm portions (electrodes L, R) and left and right lower limbs (electrodes LL, RL) for detecting electrocardiographic signals of leads I and II, and two places or the lower left sternal edge of the fourth intercostal space, and the intersection of the left anterior axillary line with a horizontal line crossing the fifth intercostal space in order to acquire electrocardiographic signals of two chest leads (V2 and V5).

From the electrocardiographic signals corresponding to the four leads including the leads I and II and two chest leads (V2 and V5) which are detected by the electrocardiogram measurement electrodes, a synthesized electrocardiogram including the remaining four chest leads V1, V3, V4, and V6 which are not actually measured by using the electrocardiogram measurement electrodes is generated by using the personal coefficients or the population coefficients.

The synthesized electrocardiogram including the chest leads V1, V3, V4, and V6 (synthesized lead vectors) can be obtained by substituting the personal or population coefficients and the electrocardiographic signals (measured lead vectors) corresponding to the four leads including the leads I and II and the two chest leads (lead V2 and lead V5) into the following determinant, and performing a matrix operation.

$$\begin{bmatrix} V1 \\ V3 \\ V4 \\ V6 \end{bmatrix} = \begin{bmatrix} T1I & T1II & T12 & T15 \\ T3I & T3II & T32 & T35 \\ T4I & T4II & T42 & T45 \\ T6I & T6II & T62 & T65 \end{bmatrix} \begin{bmatrix} VI \\ VII \\ V2 \\ V5 \end{bmatrix} \quad \text{(Exp. 1)}$$

where $$\begin{bmatrix} V1 \\ V3 \\ V4 \\ V6 \end{bmatrix}$$

represents the synthesized lead vectors, $$\begin{bmatrix} T1I & T1II & T12 & T15 \\ T3I & T3II & T32 & T35 \\ T4I & T4II & T42 & T45 \\ T6I & T6II & T62 & T65 \end{bmatrix}$$

represents the personal or population coefficients (conversion coefficients), and $$\begin{bmatrix} VI \\ VII \\ V2 \\ V5 \end{bmatrix}$$

represents the measured lead vectors.

In the case of a synthesized 12-lead electrocardiogram of the type C, the personal coefficients or the population coefficients are obtained in the following procedure.

In the case where personal coefficients of the patient are to be obtained, electrocardiogram measurement electrodes are attached to ten places on the body surface of the patient. The attachment places are portions where ten electrocardiographic signals of the leads I, II, V1, V2, V3, V4, V5, and V6 can be detected. The leads V1, V3, V4, and V6 which are synthesized lead vectors, and the leads I, II, V2, and V5 which are measured lead vectors can be actually measured from the ten electrocardiogram measurement electrodes. When these leads are substituted into the determinant above, personal coefficients (T1I, T1II, T12, T15, T3I, T3II, T32, T35, T4I, T4II, T42, T45, T6I, T6II, T62, and T65) of the patient can be obtained by the least square method. The personal coefficients are stored in the personal coefficient database 40 in time series for each patient and each synthesized electrocardiogram type.

In the case where population coefficients are to be obtained, average values of a plurality of conversion coefficients (T1I, T1II, T12, T15, T3I, T3II, T32, T35, T4I, T4II, T42, T45, T6I, T6II, T62 and T65) are obtained which are acquired in the above-described manner from a large unspecified number of persons belonging to a statistically significant population. The population coefficients are obtained for each sex and each age, and stored in the population coefficient database 50 for each sex, each age, and each synthesized electrocardiogram type.

In the case where a synthesized electrocardiogram of desired portions effective in diagnosing a heart disease of a patient who has a unique heart is to be obtained, electrocardiogram measurement electrodes are attached to portions selected as the most effective in diagnosing the heart disease. Personal coefficients are obtained by using the above-described principle, and then stored in the database. When electrocardiogram measurement is performed on the patient by using the personal coefficients, a custom-made synthesized electrocardiogram which is effective in diagnosing the heart disease of the patient can be accurately obtained.

The displaying section 60 displays the patient information and the synthesized electrocardiogram. The displaying section 60 includes a displaying device such as a liquid crystal display, and a printing device such as a printer, so that the patient information input through the patient information inputting section 10, and the generated synthesized electrocardiogram are displayed on the displaying device or printed out.

The communicating section 70 transmits and receives various data to and from external apparatuses for the electrocardiograph 100. For example, the communicating section 70 transmits data of the synthesized electrocardiogram waveforms to an external personal computer which is connected to a network, and receives data of lead waveforms from other electrocardiographs which are connected to the network.

The electrocardiograph controller 80 controls components of the electrocardiograph 100. The electrocardiograph controller 80 is electrically connected to the patient information inputting section 10, the patient information storing section 20, the electrocardiogram measurement electrodes 30, the personal coefficient database 40, the population coefficient database 50, the displaying section 60, and the communicating section 70.

As shown in FIG. 2, the electrocardiograph controller 80 includes an HDD (Hard Disk Drive) 81, a RAM (Random Access Memory) 82, a ROM (Read Only Memory) 83, and a CPU (Central Processing Unit) 84. These components are electrically interconnected by an internal bus 85.

The HDD 81 stores various programs including a synthesized electrocardiogram generation program 1, and various data. The synthesized electrocardiogram generation program 1 is configured so as to execute a synthesized electrocardiogram generating method which will be described below, and loaded from the HDD 81 into the RAM 82 to be executed by the CPU 84. The ROM 83 stores various data and parameters which are required in the execution of the synthesized electrocardiogram generation program 1.

In the embodiment, the electrocardiograph controller 80 functions as the lead waveform calculating unit to calculate a plurality of lead waveforms based on the lead potentials measured by the electrocardiogram measurement electrodes 30. The electrocardiograph controller 80 functions also as the population coefficient calculating unit to calculate population coefficients, and as a personal coefficient calculating unit to calculate personal coefficients. Moreover, the electrocardiograph controller 80 functions also as the lead deriving unit to perform a control so that synthesized B leads (B is an integer of one or more) of a specific patient are calculated from measured A leads (A is an integer of four or more) which are acquired by measuring an electrocardiogram of the specific patient, and an electrocardiogram of synthesized E leads in which the synthesized B leads are added to the measured A leads. Hereinafter, the synthesized electrocardiogram generating method of the embodiment will be described with reference to FIG. 3.

Figure 3:
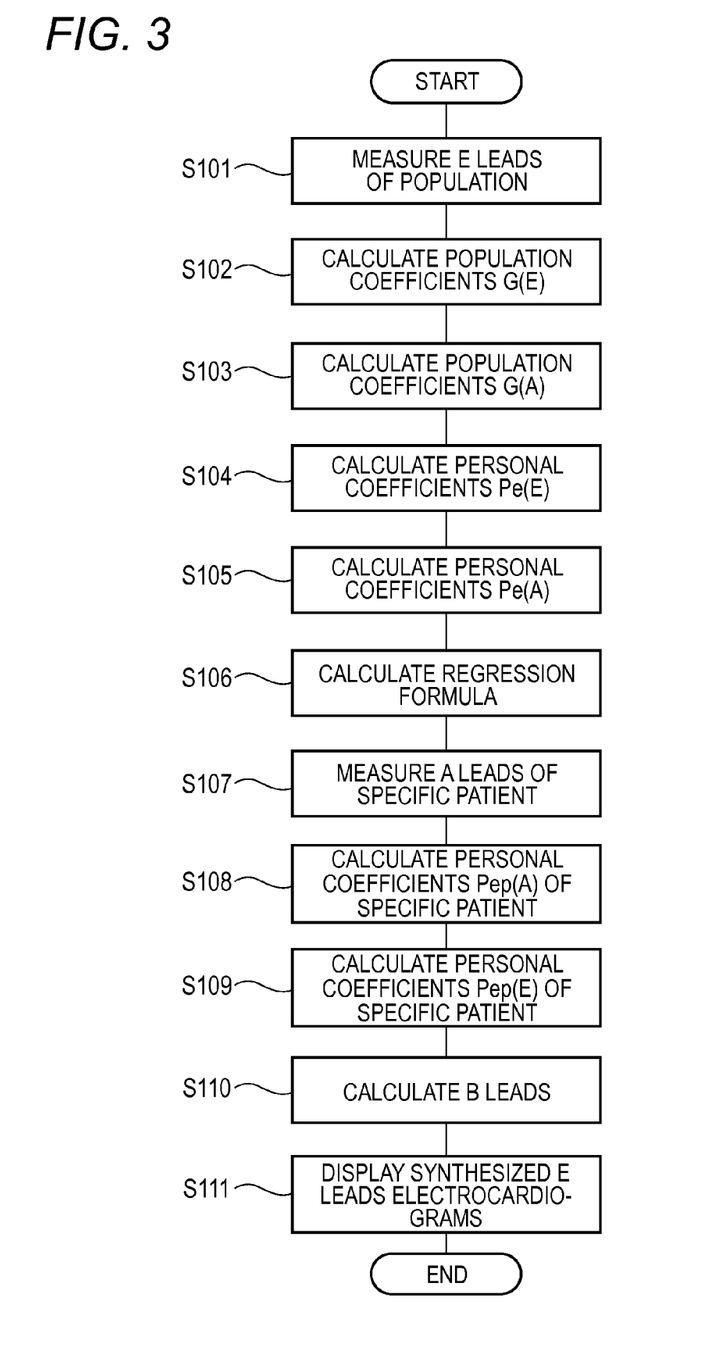
FIG. 3 is a flowchart illustrating a synthesized electrocardiogram generating method of the embodiment of the presently disclosed subject matter.

FIG. 3 is a flowchart illustrating the synthesized electrocardiogram generating method of the embodiment. In the synthesized electrocardiogram generating method of the embodiment, an operation is performed so that an A-lead electrocardiogram of a specific patient is measured, and additional B leads are synthesized based on a result of the measurement (steps S107 to S111 of FIG. 3). Before the operation, the following calculations are previously performed, or population and personal coefficients are calculated based on measured E leads which are measured with respect to a population of a predetermined number of persons, and a regression formula which is synthesized from correlations between the population and personal coefficients is calculated (steps S101 to S106 of FIG. 3).

First, the process before the operation will be described. As shown in FIG. 3, E leads of the population are measured (step S101). In the embodiment, in advance of the measurement of an A-lead electrocardiogram of the specific patient, E leads are measured with respect to the population of the predetermined number of persons. In the embodiment, the E leads are configured by the A leads and the B leads. The leads which are to be measured are requested to contain at least the A leads and the B leads, and the leads to be measure may be larger in number than the E leads. In the case where the A leads are standard 12 leads, and the B leads are additional six leads (leads V7, V8, V9, V3R, V4R, and V5R), for example, the E leads are 18 leads in which six leads are added to the standard 12 leads. The data of the measured E leads are stored in the patient information storing section 20. Preferably, the predetermined number of persons may be, for example, about 150.

Then, population coefficients G(E) are calculated (step S102). With respect to the above-described population, the electrocardiograph controller 80 calculates the population coefficients G(E) (first population coefficients) which synthesize the B leads from the A leads containing the predetermined leads in the E leads. In the case where the A leads are 12 leads, and the B leads are the six leads, for example, population coefficients G(18) which synthesize the six leads from the standard 12 leads containing the leads I, II, and V1 to V6 that function as the predetermined leads are calculated.

Then, population coefficients G(A) are calculated (step S103). By using the predetermined leads of the A leads, the electrocardiograph controller 80 calculates the population coefficients G(A) (second population coefficients) which synthesize D leads (D is A−C) from C leads (C is an integer of three or more and (A−1) or less) that are smaller in number than the A leads. In the case where the C leads are four leads of leads I, II, V2, and V4, and the D leads are eight leads containing leads III, aV (aVR, aVL, and aVF), V1, V3, V5, and V6, for example, population coefficients G(12) which synthesize the eight leads from the four leads are calculated by using the predetermined leads of the standard 12 leads.

Then, personal coefficients Pe(E) are calculated (step S104). Based on data of the E leads which are acquired in step S101, the personal coefficients Pe(E) which synthesize the B leads from the A leads are calculated with respect to each person of the population. The personal coefficients Pe(E) are generated in a number which is equal to the predetermined number of the persons. In the case where the E leads are 18 leads, and the predetermined number is 250, for example, a 250 number of personal coefficients Pe(18) are generated.

Then, personal coefficients Pe(A) are calculated (step S105). Based on data of the A leads which are contained in the data of the E leads, the electrocardiograph controller 80 calculates the second personal coefficients Pe(A) which synthesize the D leads from the C leads, with respect to each person of the population. As described above, the D leads are leads which are obtained subtracting the C leads from the A leads. The personal coefficients Pe(A) are generated in a number which is equal to the predetermined number of the persons. In the case where the A leads are 12 leads, and the predetermined number is 250, for example, a 250 number of personal coefficients Pe(12) are generated.

Next, the regression formula is calculated (step S106) Based on the population coefficients G(E), G(A) and the personal coefficients Pe(E), Pe(A) for the predetermined number of the persons, the electrocardiograph controller 80 calculates a regression formula for the first personal coefficients Pe(E) to the second personal coefficients Pe(A).

In the embodiment, it is assumed that the population coefficients G(E), G(A) which are calculated from a population of a predetermined number of persons are correlated with the personal coefficients Pe(E), Pe(A) for the specific patient. Specifically, it is assume that following Expression (2) holds.

$$G(E):G(A)=Pe(E):Pe(A) \quad \text{(Exp. 2)}$$

Namely, it is contemplated that relationships which are similar to those between large leads (E leads) and small leads (A leads) relevant to the population coefficients exist between large leads (E leads) and small leads (A leads) relevant to the personal coefficients.

Among the four variables G(E), G(A), Pe(E), and Pe(A) in Expression (2) above, the variables G(E) and G(A) can be calculated in steps S102 and S103, and Pe(A) is a variable which can be calculated by actually measuring the A leads. Therefore, G(E), G(A), and Pe(A) in the four variables are known variables. Assuming that the three variables G(E), G(A), and Pe(A) are known, the electrocardiograph controller 80 calculates, for example, a regression formula for obtaining Pe(E) as shown in Expression (3) below.

$$Pe(E)=G(E)*Pe(A)/G(A) \quad \text{(Exp. 3)}$$

In this way, a regression formula for the personal coefficients Pe(E) to the personal coefficients Pe(A) when points which are expressed by the personal coefficients Pe(E) and Pe(A) for each person of the population are plotted on an XY plane is calculated. According to Expression (3) above, it is said that the personal coefficients Pe(E) are a conversion coefficients which are obtained by comparing the personal coefficient Pe (A) and the population coefficient G(A) with each other, and correcting the population coefficient G(E) based on a result of the comparison.

Next, the process in the operation will be described. First, the A leads of the specific patient are measured (step S107). The electrocardiograph controller 80 measures the A leads of the specific patient, and stores data of measured leads in the patient information storing section 20.

Then, personal coefficient Pep (A) of the specific patient are calculated (step S108). By using the measurement data of the A leads which are acquired in step S107 above, the electrocardiograph controller 80 calculates the personal coefficients Pep(A) for calculating the D leads from the C leads. In the case where the C leads are four leads of leads I, II, V2, and V4, and the D leads are eight leads containing leads III, aV, V1, V3, V5, and V6, for example, personal coefficients Pep(12) which synthesize the eight leads from the four leads are calculated by using the measured standard 12 leads.

Then, personal coefficients Pep(E) of the specific patient are calculated (step S109). The electrocardiograph controller 80 applies the population coefficients G(E) and G(A) which are calculated in steps S102 and S103 above, and the personal coefficients Pep(A) of the specific patient which are calculated in step S108 above, to the regression formula of Expression (3) above, to calculate the personal coefficients Pep(E) of the specific patient. In the case where the A leads are the standard 12 leads, and the E leads are 18 leads, for example, following Expression (4) is obtained.

$$Pep(18)=G(18)*Pep(12)/G(12) \quad \text{(Exp. 4)}$$

In the embodiment, as described above, A leads of a specific patient are measured during an operation, and the personal coefficients Pep(12) of the specific patient are calculated based on a result of the measurement. Then, the population coefficients G(E) and G(A) which are calculated before the operation, and the personal coefficients Pep(12) which are calculated during the operation are applied to Expression (4) above, thereby calculating the personal coefficients Pep(18). The personal coefficients Pep(18) are conversion coefficients which are obtained by correcting the population coefficients G(18) according to a result of comparison of the personal coefficients Pep(12) containing features (referred to as physique factor) of the specific patient, with the population coefficients G(12). Therefore, the personal coefficients Pep(18) may possibly be conversion coefficients which are more suitable to the actual state of synthesized electrocardiograms of the specific patient as compared with the population coefficients G(18).

Then, the B leads are synthesized (step S110). The electrocardiograph controller 80 synthesizes the B leads from the A leads measured in step S107, by using the personal coefficients Pep(18).

Then, a synthesized E leads electrocardiogram is displayed (step S111). The electrocardiograph controller 80 controls the displaying section 60 so as to display the synthesized E leads electrocardiogram. In response to instructions from the electrocardiograph controller 80, the displaying section 60 displays the synthesized E leads electrocardiogram or prints the electrocardiogram by the printer.

In the embodiment, as described above, the preprocessing before the operation is performed in the following manner. Lead potentials of living body portions are measured, and a plurality of lead waveforms are calculated based on the measured lead potentials. With respect to a population of a predetermined number of persons, then, the population coefficients G(E) for deriving the additional B leads from the A leads containing a predetermined lead waveform in the plurality of lead waveforms, and the population coefficients G(A) for deriving the additional D leads from the C leads in which the number of lead waveforms is smaller than that in the A leads are calculated.

With respect to each person of the population, moreover, the personal coefficients Pe(E) for deriving the B leads from the A leads, and the personal coefficients Pe(A) for deriving the D leads from the C leads are calculated, and a relationship between the magnitude of a ratio of the population coefficients G(E) to the population coefficients G(A), and that of a ratio of the personal coefficients Pe(E) to the personal coefficients Pe(A) are calculated.

Moreover, A leads of a specific patient are acquired in electrocardiogram measurement, personal coefficients Pep(A) are calculated based on the A leads, and personal coefficients Pep(E) of the specific patient are calculated based on the above-described relationship and the personal coefficients Pep(A). Furthermore, B leads of the specific patient are synthesized by using the personal coefficients Pep(A).

The electrocardiograph, and method and program for generating a synthesized electrocardiogram of the embodiment which have been described above have the following effects.

The population coefficients for deriving desired leads are corrected based on known personal coefficients including the physique factor of a specific patient, and hence it is possible to calculate conversion coefficients to which the physique factor of the specific patient are reflected, and which have a high accuracy of synthesized leads. Therefore, the accuracy of desired synthesized leads can be sufficiently ensured while avoiding the burden of previously measuring leads of arbitrary portions of the patient himself/herself in order to calculate personal coefficients for deriving desired leads.

The operation method of the electrocardiograph of the embodiment is similar to that of, for example, a related-art standard 12-lead electrocardiograph. After execution of standard 12-lead electrocardiogram examination, therefore, additional leads can be synthesized without replacing electrodes or with no change, and then recorded and displayed. Consequently, a medical person can immediately analyze the displayed synthesized electrocardiogram, and rapidly start diagnosis.

In the embodiment, the electrocardiograph and the synthesized electrocardiogram generating method and program have been described. In the invention, it is a matter of course that those skilled in the art can made various additions, modifications, and omissions within the technical scope of the invention.

In the embodiment, for example, the case where the electrocardiograph includes the population coefficient database and the personal coefficient database has been described. However, another configuration may be possible where a population coefficient database and a personal coefficient database are disposed outside an electrocardiograph, and data of population and personal coefficients are written and read via a network.

Although the embodiment has been described assuming that a human being is the measurement object for an electrocardiogram, the measurement object is not limited to a human being but may be an animal.

In the embodiment, the case has been described where the electrocardiograph controller includes the HDD, the RAM, the ROM, and the CPU, and the CPU executes the synthesized electrocardiogram generating program to control the components of the electrocardiograph. The program may be stored in a non-transitory computer-readable recording medium. Alternatively, a configuration may be possible where the electrocardiograph controller includes an FPGA (Field-Programmable Gate Array) or an ASIC (Application Specific Integrated Circuit), and the components of the electrocardiograph are controlled by hardware.

According to the presently disclosed subject matter, the population coefficients for deriving desired leads are corrected based on known personal coefficients containing features of a specific subject, and hence it is possible to calculate conversion coefficients to which the features of the specific subject are reflected, and which have a high accuracy of synthesized leads. Therefore, the accuracy of desired synthesized leads can be sufficiently ensured while avoiding the burden of previously measuring leads of arbitrary portions of the subject himself/herself in order to calculate personal coefficients for deriving the desired leads.

What is claimed is:
1. An electrocardiogram measuring apparatus comprising:
a lead waveform calculating unit which is configured to calculate a plurality of lead waveforms based on measured lead potentials of living body portions, the plurality of lead waveforms including A-lead waveforms and B-lead waveforms, wherein A is an integer of four or more and B is an integer of one or more, and the A-lead waveforms consisting of C-lead waveforms and D-lead waveforms, wherein C is an integer of three or more but less than A and D is A−C;
a population coefficient calculating unit which is configured to calculate:
first population coefficients for a population of a predetermined number of persons which synthesize the B-lead waveforms from the A-lead waveforms; and
second population coefficients for the population which synthesize the D-lead waveforms from the C-lead waveforms by using the A-lead waveforms;
a personal coefficient calculating unit which is configured to calculate:
first personal coefficients for each person of the population which synthesize the B-lead waveforms from the A-lead waveforms, the first population coefficients being averages of the first personal coefficients; and
second personal coefficients for each person of the population which synthesize the D-lead waveforms from the C-lead waveforms, the second population coefficients being averages of the second personal coefficients; and a lead deriving unit which is configured to:
calculate first personal coefficients of a specific subject based on:
a relationship between a magnitude of a ratio of the first population coefficients to the second population coefficients, and a magnitude of a ratio of the first personal coefficients to the second personal coefficients; and
second personal coefficients of the specific subject which are calculated based on A-lead waveforms of the specific subject, the A-lead waveforms being acquired by electrocardiogram measurement;
synthesize B-lead waveforms of the specific subject by using the first personal coefficients of the specific subject; and
add the B-lead waveforms of the specific subject to the A-lead waveforms of the specific subject to generate a synthesized electrocardiogram.

2. The electrocardiogram measuring apparatus according to claim 1, wherein the lead deriving unit is configured to:
calculate a regression formula for the first personal coefficients to the second personal coefficients when points which are expressed by the first and second personal coefficients for each person of the population are plotted on an XY plane; and
apply the second personal coefficients of the specific subject to the regression formula to calculate the first personal coefficients of the specific subject.

3. The electrocardiogram measuring apparatus according to claim 1, wherein
the A-lead waveforms are 12-lead waveforms containing six limb lead waveforms I, II, III, aVR, aVL, and aVF, and six chest lead waveforms V1, V2, V3, V4, V5, and V6, and
the B-lead waveforms are six-lead waveforms containing lead waveforms of V7, V8, V9, V3R, V4R, and V5R.

4. The electrocardiogram measuring apparatus according to claim 1, wherein the lead potential measuring unit is configured to measure lead potentials in 18 measurement portions of an electrocardiogram, and the lead waveform calculating unit is configured to calculate 18 lead waveforms based on the measured 18 lead potentials.

5. The electrocardiogram measuring apparatus according to claim 1, wherein the first population coefficients and the second population coefficients are stored in a population coefficient database, and the first personal coefficients and the second personal coefficients are stored in a personal coefficient database.

6. A synthesized electrocardiogram generating method comprising:
measuring lead potentials of living body portions, and calculating a plurality of lead waveforms based on the measured lead potentials, the plurality of lead waveforms including A-lead waveforms and B-lead waveforms, wherein A is an integer of four or more and B is an integer of one or more, and the A-lead waveforms consisting of C-lead waveforms and D-lead waveforms, wherein C is an integer of three or more but less than A and D is A–C;

calculating:
first population coefficients for a population of a predetermined number of persons which synthesize the B-lead waveforms from the A-lead waveforms; and
second population coefficients for the population which synthesize the D-lead waveforms from the C-lead waveforms by using the A-lead waveforms;

calculating:
first personal coefficients for each person of the population which synthesize the B-lead waveforms from the A-lead waveforms, the first population coefficients being averages of the first personal coefficients; and
second personal coefficients for each person of the population which synthesize the D-lead waveforms from the C-lead waveforms, the second population coefficients being averages of the second personal coefficients;

calculating a relationship between a magnitude of a ratio of the first population coefficients to the second population coefficients, and a magnitude of a ratio of the first personal coefficients to the second personal coefficients;

acquiring A-lead waveforms of a specific subject by electrocardiogram measurement, and calculating second personal coefficients of the specific subject based on the A-lead waveforms of the specific subject;

calculating first personal coefficients of the specific subject based on the relationship and the second personal coefficients of the specific subject;

deriving B-lead waveforms of the specific subject by using the first personal coefficients of the specific subject; and adding the B-lead waveforms of the specific subject to the A-lead waveforms of the specific subject to generate a synthesized electrocardiogram.

7. The synthesized electrocardiogram generating method according to claim 6, wherein, in a process of calculating the first personal coefficients of the specific subject, a regression formula for the first personal coefficients to the second personal coefficients when points which are expressed by the first and second personal coefficients for each person of the population are plotted on an XY plane is calculated, and the second personal coefficients of the specific subject is applied to the regression formula to calculate the first personal coefficients of the specific subject.

8. A non-transitory computer-readable recording medium storing the synthesized electrocardiogram generating program causing an electrocardiogram measuring apparatus to execute the synthesized electrocardiogram generating method according to claim 6.

* * * * *